United States Patent [19]

Lang et al.

[11] 4,364,629
[45] Dec. 21, 1982

[54] OPERATION MICROSCOPE HAVING A SMALL WORKING DISTANCE

[75] Inventors: Walter H. Lang; Franz Muchel, both of Konigsbronn, Fed. Rep. of Germany

[73] Assignee: Carl Zeiss-Stiftung, Oberkochen, Fed. Rep. of Germany

[21] Appl. No.: 148,968

[22] Filed: May 12, 1980

[30] Foreign Application Priority Data

May 16, 1979 [DE] Fed. Rep. of Germany ....... 2919678

[51] Int. Cl.³ .............................................. G02B 21/20
[52] U.S. Cl. .................................... 350/516; 350/520; 350/573
[58] Field of Search ....................... 350/18, 33, 36, 38, 350/54, 145, 235

[56] References Cited

U.S. PATENT DOCUMENTS

| 737,844 | 9/1903 | Hubbard | 350/18 |
|---|---|---|---|
| 3,123,984 | 3/1965 | Vogl | 350/36 |
| 4,061,135 | 12/1977 | Widran et al. | 350/36 X |

FOREIGN PATENT DOCUMENTS 954629  4/1964  United Kingdom ................. 350/54

Primary Examiner—John K. Corbin
Assistant Examiner—Matthew W. Koren
Attorney, Agent, or Firm—Hopgood, Calimafde, Kalil, Blaustein & Judlowe

[57] ABSTRACT

The invention contemplates a modular system of interchangeable and multiply-combinable objective-lens components for selective use with an operation microscope to enable improved viewing of small operational areas, particularly in areas which are in deep channels or recesses. The construction permits optional use of the instrument in the context of stereoscopic or split-beam binocular viewing, or as an endoscope. Viewing is enhanced by efficient light transmission of both (a) the light used for object illumination and (b) the optical transmission of the image to be viewed.

13 Claims, 6 Drawing Figures

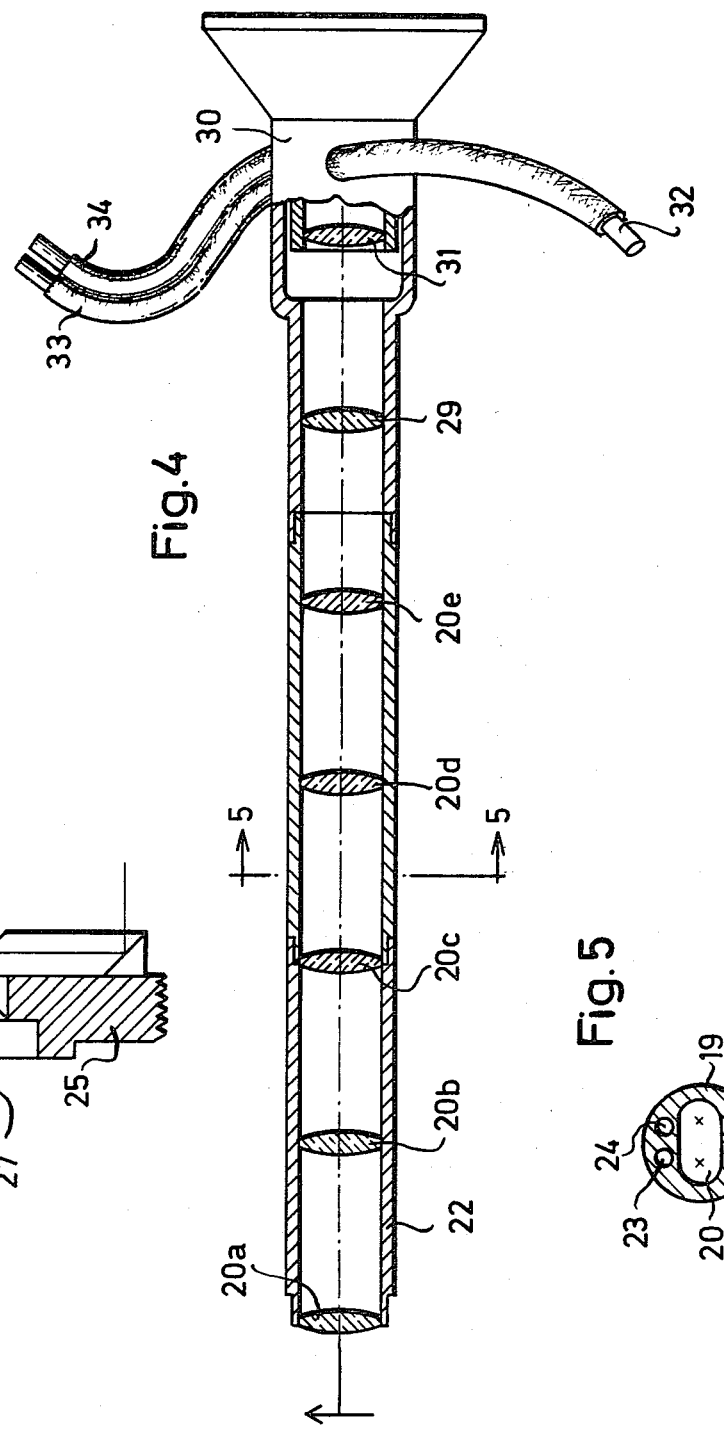

OPERATION MICROSCOPE HAVING A SMALL WORKING DISTANCE

BACKGROUND OF THE INVENTION

This invention relates to an operation microscope of small working distance, intended particularly for operations in narrow and deep operation channels.

Operation microscopes are stereomicroscopes which are held in suitable manner on supporting arms and couplings for microsurgical operations. In order that the surgeon shall not be impeded by the microscope in the guidance of his microsurgical instruments, a minimum free working distance is necessary from the front surface of the operation microscope to the operation field. Depending on the specialty and the operation to be effected, the working distance is between 100 and 400 mm. For undisturbed observation and illumination, a relatively large conical region within which the ray paths extend must be kept free in front of the objective.

For operations in narrow and deep operation channels such as are a matter of course, for instance, in microsurgery on the vocal cords or on intervertebral disks, it may, however, happen that the illuminating ray path is in part cut off in the operation channel and by reason of the microsurgical instruments introduced therein. As a result, available illumination in the operating area is reduced. Of much greater importance, however, is the fact that both observation ray paths may be partly blocked; and in the extreme case, only a single observation ray path can be used. Such circumstances handicap the surgeon by eliminating one of his most important prerequisites, namely, sufficiently good stereo observation, for location of depth in the operating area and for proper guidance of microsurgical instruments.

A radial reduction in size of the illuminating or observation cone by increase of the working distance is generally not possible (1) due to the reduction in the angle of convergence inherent therein, which angle should be as large as possible for the sake of good stereo observation, and (2) due to the characteristically rather low aperture of objectives in operation microscopes.

It is known from German Provisional Patent (Auslegeschrift) No. 2,309,203 to provide a conical cover or shield for the region which is to be kept free for the ray path. This purely mechanical measure, to be sure, prevents cutting off of the ray paths by surgical instruments but nevertheless does not increase the space available for manipulation. An objective provided with such a cover is not suitable for introduction into long cylindrical openings. Further, what has been stated above with respect to the angle of convergence and low aperture also applies.

In general, rigid or flexible endoscopes are used for microscopic observations in deep or narrow body openings. However, relatively few endoscopes are known which permit stereoscopic observation.

German Pat. No. 2,354,370 describes such an endoscope which consists of two flexible individual endoscopes coupled by a clamp, but it is suitable only for introduction in the nostrils. U.S. Pat. No. 3,520,587 also describes a flexible stereo endoscope which contains two separate image-conducting fiber bundles in a surrounding tube.

Flexible endoscopes are, however, only poorly suited for observation of operating areas since their image quality, even in the case of very good image conductors, is fundamentally poorer than that of operation microscopes, due to the structure of the individual-fiber arrangements, and also due to split or completely broken fibers. Their advantage of flexibility is furthermore not required in operation microscopy; on the contrary, such flexibility can have a detrimental effect as a result of image instability.

A rigid endoscope for stereo photography is known from German Unexamined Patent Application (Offenlegungsschrift) No. 1,766,803 and from German Gebrauchsmuster No. 1,996,605. This instrument has an elongated base body in which two parallel optical systems are arranged, and in which the proximal end bears a stereo attachment for binocular observation or for stereo photography. The doubled design of the observation channel and the resultant additional centering work within the channel, as well as of the two channels with respect to each other, make this instrument rather expensive to manufacture.

Furthermore, all endoscopes have the disadvantage that, in accordance with their purpose, they are to be manually guided by the user, so that only one hand remains free for operating the adjustment elements and handling the surgical instruments. When a television camera or a co-observer tube is attached as is frequently the case with operation microscopes, an endoscope, for the reasons indicated above, would now be in two senses very difficult to handle.

BRIEF STATEMENT OF THE INVENTION

The object of the present invention is to provide an operation microscope which, without blocking off the optical ray paths, permits manipulation by both hands in narrow and deep operation channels.

This object is achieved in accordance with the invention by the provision of bar-shaped interchangeable objectives of short focal length by which the observation ray paths are brought to the object of examination.

The advantage of the invention resides in the fact that interchangeable objectives of small working distance and thus high aperture and with large angle of convergence may be used for stereoscopic observation, without allowing a reduction in working distance to become a limitation on the operator's freedom of manipulation.

It is advantageous to provide channels in the objective housing for the passage of surgical instruments and for the flushing of the operating area. The patient is protected by such guidance of instruments, and the surgeon's guidance of longer instruments is facilitated; and the use of such a channel for flushing purposes enables a free view of the object to be handled.

By the use of only one viewing channel for the transmission of both stereoscopic ray paths, objectives are easy and cheap to manufacture. Furthermore, such objectives can be fastened by simple means to special monocular tubes, as a result of which there is obtained a rigid endoscope of extremely high light efficiency.

Since a plurality of interchangeable objectives with different structural lengths and linear magnifications are provided, a thus-equipped operation microscope is of universal use. The same is true of the endoscope use outlined above.

Interchangeable lenses of the invention can be inserted in particularly economical fashion if several of them can be combined end-to-end to form a longer objective. For example, it is advantageous to provide each microscope with several individual objectives of different structural length and constant linear magnification, as well as several individual objectives of constant short structural length and different linear magnifications, thus permitting universal use of the operation microscope with the fewest possible accessories.

Variable magnification during the operation can be obtained by the use of vario-oculars or by switchable-tube optical systems.

DETAILED DESCRIPTION

The invention will be explained in further detail by way of example with reference to the accompanying drawings, in which:

FIG. 2a is a sectional view of a replaceable beam splitter for the operation microscope of FIG. 1;

FIG. 4 is a sectional view to show the use of interchangeable objectives of the type shown in FIG. 1, but interconnected serially for an endoscope use; and FIG. 5 is a transverse sectional view through an illustrative interchangeable objective, as at 5—5 in FIG. 1.

Figure 1:
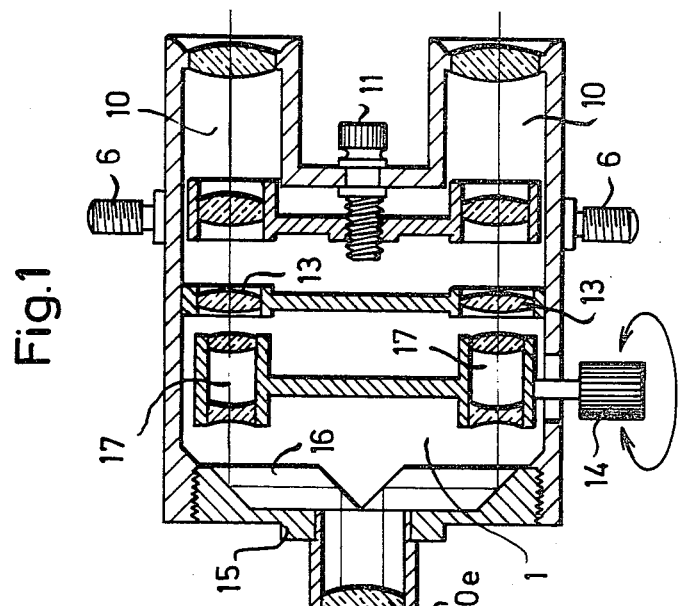
FIG. 1 is a simplified longitudinal sectional view through one embodiment of an operation microscope of the invention.

The operation microscope shown in FIG. 1 consists of a housing 1 which is held in tiltable and swingable manner by means of two threaded bolts 6 on supporting arms (not shown). The housing 1 contains the optical system necessary for stereoscopic viewing, consisting of oculars 10, each of which contains a lens member which is displaceable axially via a common line adjustment 11 by which the intermediate image produced by tube lenses 13 can be continuously after-enlarged. A change of the linear magnification in fixed larger steps is possible by means of a turret 14, which permits different lens combinations 17 to be swung into the two ray paths.

The attachments customary on operation microscopes for concurrent multiple observation and documentation have not been shown. They include, for instance, beam splitters in order to properly split the observation ray path, and attachments for connection of a 35-mm camera, a television camera and one or more co-observer tubes.

In the front part of the housing 1, there is removably fastened an adapter 15 which contains two prisms 16 by which the observation base can be reduced in size and to which there is attached a bipartite assembly of bar-shaped interchangeable lens modules 2, 12.

Figure 2B:
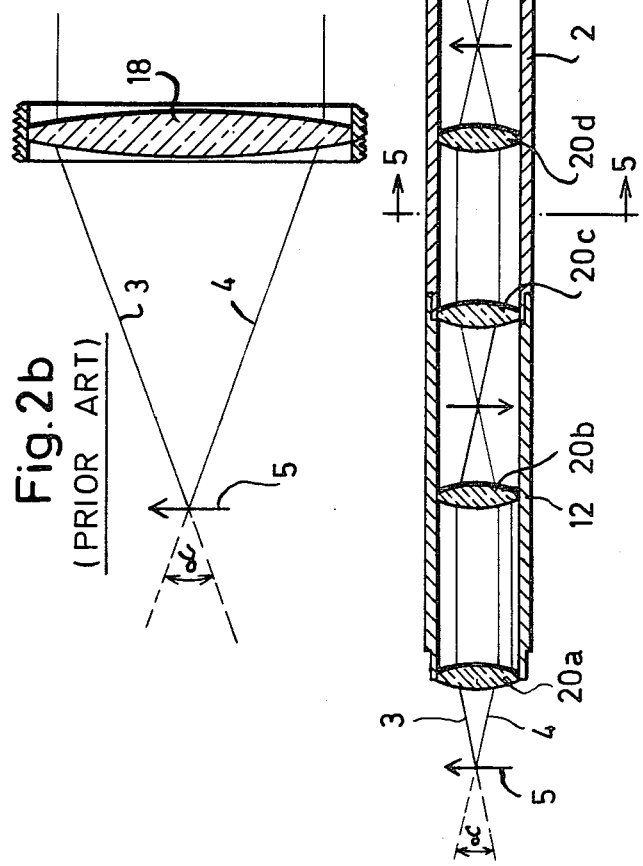
FIG. 2b is a sectional view of an interchangeable objective for traditional operation microscopes, said view being labeled "Prior Art"

The adapter 15 is replaceable by the interchangeable objective 18 shown in FIG. 2b. After the screwing of the objective 18 into the housing 1 there is obtained an operation microscope of traditional construction which can be used, for instance, to advantage for the examination of larger flat object fields (dermatology) and therefore in cases in which the bar-shaped interchangeable objective modules are not required.

The adapter 15, however, can also be replaced by the adapter 25 shown in FIG. 2a in which a prism system 26 is so arranged that a splitting up of the ray path 27 is effected for binocular observation. By means of this adapter 25, to which the interchangeable objective modules 2, 22 can also be removably attached, the operation microscope can be optionally used in cases in which good stereo observation is less important than high resolution of flat objects in body cavities.

The interchangeable objectives (or objective modules), 2, 12, 22 which can be used in either the stereoscopic or the split-ray viewing mode have the shape of elongated cylinders of circular cross section. In addition to the imaging-lens system shown in FIG. 1, these objective modules also contain channels 23, 24 (FIG. 5) through which liquids can be conducted for selective rinsing of the object space. Furthermore, a glass-fiber bar 21 via which the object space can be illuminated is arranged in the objectives.

The lens members 20a–20e which form several intermediate images of the object have an oval cross-section whereby a suitable compromise is obtained between the need for the smallest possible outside diameter of the objectives and the largest possible angle of convergence for stereo observation.

Figure 3:
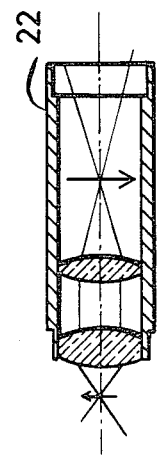
FIG. 3 is a sectional view of an interchangeable objective module for the operation microscope of the invention.

Instead of the objective module 12, it is also possible to use an objective module 22 as shown in FIG. 3. As suggested by arrows, objective 22 has a larger linear magnification, in addition to a shorter structural shape. Of course, the operation microscope shown in FIG. 1 can also be used without the objectives 12 and 22 and merely with the objective 2. After the removal of the objective 12, an image reversal takes place which, however, can be avoided by designing the objectives to be replaced in all cases for positive linear magnification or by arranging additional image-reversing means (in selectively switchable manner) within the tube 1.

FIG. 4 shows use of the objectives (or objective modules) 2, 22 as an endoscope. For this purpose, they are connected with a tube 30 which contains a lens 29 for the formation of an intermediate image of the object, as well as a vario-ocular 31. The hoses 33 and 34 are connected with the channels 23 and 24 in the objectives. For the illuminating of the object, the flexibly extended fiber bundle 32 is connected to a suitable source or sources of light.

In order to facilitate the guidance of the endoscope for the user, the instrument can be mounted in an easily movable manner on supporting arms. And it will be understood that means for beam-splitting and for connecting of co-observation or documentation systems can be provided in the tube 30.

What is claimed is:

1. An operation-microscope kit, comprising a binocular viewing module having a viewing end and an objective-attachment end, said objective-attachment end being adapted for detachable connection to a conventional objective lens of relatively large diameter for operation upon object areas that are relatively exposed and uncluttered, an adapter module adapted for detachable connection to the objective-attachment end of said viewing module, said adapter module having a central region adapted for detachable connection to an objective-lens mount of reduced diameter substantially less than said large diameter and said adapter module having prism means for folding the binocular-viewing axes to within the lesser-diameter capacity of said central region, and one or more objective-lens modules of substantially said reduced diameter and adapted for detachable connection to each other and to said objective-lens mount in end-to-end relation.

2. An operation-microscope kit according to claim 1, in which each of said one or more objective-lens modules is bar-shaped and of relatively short focal length.

3. An operation-microscope kit according to claim 1, characterized by the fact that each objective-lens module is adapted for use in the transmission of the two observation ray paths (3, 4) necessary for stereoscopic viewing.

4. An operation-microscope kit according to claim 1, characterized by the fact that each objective-lens module contains lens means in a tubular housing adapted for detachable connection to the tubular housing of another such objective-lens module, and means within the tubular housing by which an illuminating ray path may be guided to the outermost end of one or more thus-connected objective-lens modules.

5. An operation-microscope kit according to claim 1, characterized by the fact that each objective-lens module contains lens means in a tubular housing adapted for detachable connection to the tubular housing of another such objective-lens module, and that axially extending channels (23, 24) within each module establish channels through which liquids may be conducted for flushing the object-viewing area beyond the outermost end of one or more thus-connected objective-lens modules.

6. An operation-microscope kit according to claim 1, characterized by the fact that each objective-lens module contains lens means in a tubular housing adapted for detachable connection to the tubular housing of another such objective-lens module, and that one or more axially extending channels (23, 24) within each module establish guide means for the manipulable passage of one or more micro-surgical instruments.

7. An operation-microscope kit according to claim 1, characterized by the fact that a plurality of interchangeable objective-lens modules (2, 12, 22) of different structural length are provided.

8. An operation-microscope kit according to claim 1, characterized by the fact that said one or more objective-lens modules include a plurality of interchangeable lens modules (2, 12, 22) of shorter structural length which can be combined to form an interchangeable objective of larger structural length.

9. An operation-microscope kit according to claim 1, characterized by the fact that said one or more objective-lens modules include interchangeable objective-lens modules (2, 12, 22) of different working distances and different linear magnification.

10. An operation-microscope kit according to claim 1, characterized by the fact that one of said objective-lens modules includes a vario-ocular (31) selectively usable in combination with other of said one or more objective-lens modules (2, 12, 22).

11. An operation-microscope kit according to claim 1, characterized by an additional adapter module (25) interchangeable with said first-mentioned adapter module and containing means for pupil splitting for pure binocular observation.

12. An operation-microscope kit according to claim 1, characterized by the fact that one of said objective-lens modules includes means for splitting the observation ray path for purposes of co-observation and documentation.

13. An operation-microscope kit according to claim 1, characterized by the fact that each objective-lens module contains lens means in a tubular housing adapted for detachable connection to the tubular housing of another such objective-lens module, and that the effective focal length for each particular objective-lens module is less than the structural length of the particular module.

* * * * *